United States Patent [19]
Wise et al.

[11] 4,115,565
[45] Sep. 19, 1978

[54] 6,7-DIMETHOXY-2-(4-THIOMOR-PHOLINYL)-4-QUINAZOLINAMINE AND RELATED SULFOXIDE AND SULFONE

[75] Inventors: Lawrence D. Wise; Glenn C. Morrison, both of Ann Arbor, Mich.

[73] Assignee: Warner-Lambert Company, Morris Plains, N.J.

[21] Appl. No.: 844,755

[22] Filed: Oct. 25, 1977

Related U.S. Application Data

[63] Continuation-in-part of Ser. No. 759,695, Jan. 17, 1977, abandoned.

[51] Int. Cl.$^2$ .................. A61K 31/505; C07D 417/04

[52] U.S. Cl. ........................................ 424/246; 544/58; 544/62

[58] Field of Search ...................... 424/246; 544/62, 58

[56] References Cited

U.S. PATENT DOCUMENTS 3,681,340  8/1972  Rodriguez et al. ................. 544/62 X

*Primary Examiner*—Richard L. Raymond
*Attorney, Agent, or Firm*—Albert H. Graddis; Frank S. Chow; George M. Yahwak

[57] ABSTRACT

Disclosed are a series of quinazoline derivatives which have activity as hypotensive agents.

5 Claims, No Drawings

6,7-DIMETHOXY-2-(4-THIOMORPHOLINYL)-4-QUINAZOLINAMINE AND RELATED SULFOXIDE AND SULFONE

This application is a continuation-in-part application of U.S. Ser. No. 759,695, filed Jan. 17, 1977, now abandoned.

This invention relates to quinazoline derivatives having the following formula:

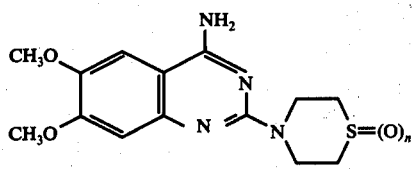

wherein $n$ is 0, 1 or 2.

Related compounds have been described in the literature. For example, the above compounds are pharmacologically related to Prazosin (IV) which is disclosed in U.S. Pat. No. 3,511,836 and which has the formula:

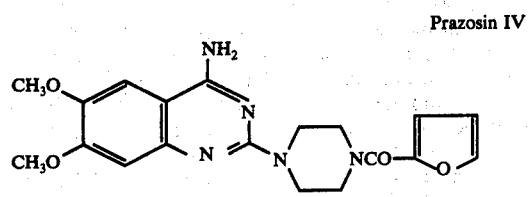

Prazosin IV

Examples 1 and 3 may be prepared by reaction of chloroquinazoline V with thiomorpholine or thimorpholine S,S-dioxide, respectively. The synthesis of V chloraquinazoline is described by F. H. S. Curd, et al., *J. Chem. Soc.*, 1759 (1948).

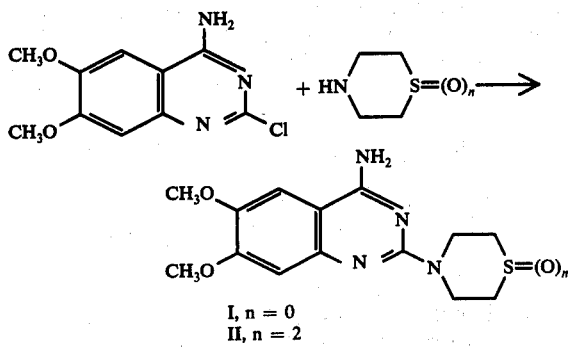

I, n = 0
II, n = 2

The sulfoxide (example 2) may be prepared by treatment of example 1 with one equivalent of a suitable oxidizing agent such as m-chloroperbenzoic acid.

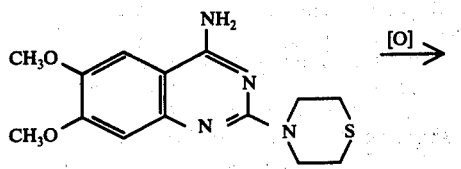

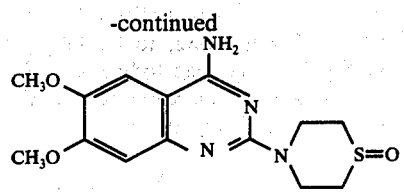

In another aspect of the invention, there is provided a pharmaceutical composition comprising a compound of formula I as has been defined or a pharmaceutically acceptable salt thereof together with a pharmaceutically acceptable carrier.

The pharmaceutically acceptable salts of the free compounds of general formula I may be prepared by conventional reactions with equivalent amounts or inorganic or organic acid solutions. As exemplary of pharmaceutically acceptable salts there are the salts of hydrochloric, hydrobromic, sulfuric, benzenesulphonic, acetic, oxalic, malic, and citric acids.

The compounds of general formula I, as well as their pharmaceutically acceptable inorganic and organic acid salts, may be administered enterally of parenterally in admixture with a liquid or solid pharmaceutical diluent or carrier. As injection medium it is preferred to use water which contains the conventional pharmaceutical adjuvants for injection solutions such as stabilizing agents, solubilizing agents and buffers, for example, ethanol, complex-forming agents such as ethylene diamene tetraacetic acid, tartrate, and citrate buffers and highly molecular weight polymers such as polyethylene oxide for viscosity regulation. Examples of carrier materials include starch, lactose, mannitol, methylcellulose, talc, highly dispersed silicic acids, high molecular weight fatty acids such as stearic acid, and high molecular weight polymers such as polyethylene glycols. Oral forms of administration may, of course, contain flavoring, sweetening, preserving, suspending, thickening, or emulsifying agents.

A particular aspect of the formula composition comprises a compound of formula I in an effective unit dose form. By "effective unit does" is meant a predetermined amount sufficient to be effective to bring about the desired hypotensive reaction.

In yet a further aspect of the invention, there is provided a method of producing a hypotensive action in mammals, including man, which comprises the administration of an effective depressant amount of a compound of general formula I or a pharmaceutically acceptable salt thereof.

The dosage of the compounds of formula I or their pharmaceutically acceptable salts depends, of course, on the nature and severity of the excitability to be countered, as well as the path of administration. When tested in spontaneously hypertensive rats to determine hypotensive activity, the compound of example I for example, was active at a dose of 10 mg/kg and the compound of example 3 was active at a dose of 30 mg/kg. The compounds and their pharmaceutically acceptable salts are active as hypotensives in mammals when administered orally, parenterally, or intravenously throughout a dose range of 1.0 – 100.0 mg/kg of mammalian body weight, preferably in the range of 5.0 – 50.0 mg/kg. In addition, these compounds appear to have less undesirable α-blocking activity than Prazosin.

It is believed that one of ordinary skill in the art, can, using the preceding description, utilize the present invention to its fullest extent. The following specific embodiments, are, therefore, to be simply construed as merely illustrative and not to limit the remainder of the specification and claims in any way whatsoever.

EXAMPLE 1

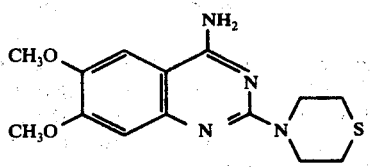

6,7-Dimethoxy-2-(4-thiomorpholinyl)-4-quinazolinamine

A mixture of 8.00 g of 2-chloro-6,7-dimethoxy-4-quinazolinamine and 6.90 g. of thiomorpholine in 80 ml of chlorobenzene was refluxed for 18 hrs. The reaction mixture was cooled to room temperature, and the precipitate was collected. There was deposited 8.00 g (70.2%) of white powder, mp 267°–269°, dec. The product was recrystallized from methanol to give an analytical sample, mp 270°–271°, dec.

Anal. Calcd for $C_{14}H_{18}N_4O_2S.HCl$: C, 49.05; H, 5.59; Cl, 10.34; N, 16.34; S, 9.35. Found: C, 48.91; H, 5.59; Cl, 10.53; N, 16.18; S, 9.51.

EXAMPLE 2

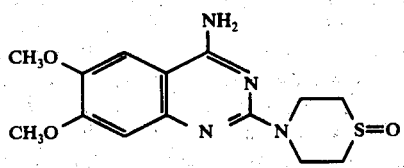

6,7-Dimethoxy-2-(4-thiomorpholinyl)-4-quinazolinamine S-oxide

To a solution of 1.00 g of 6,7-dimethoxy-2-(4-thiomorpholinyl)-4-quinazolinamine in 100 ml of methylene chloride at 0° was added dropwise over 15 min. a solution of 0.66 g of 85% m-chloroperbenzoic acid in 25 ml of methylene chloride. After an additional 2 hrs. at 0°, the reaction mixture was washed with dilute sodium bicarbonate and water. The organic extracts were dried over anhydrous sodium sulfate, and the solvent was evaporated. There remained 0.75 g (71.4%) of white powder, mp 278°–280°, dec. Recrystallization from methylene chloride-isopropanol gave an analytical sample, mp 283°–285°, dec.

Anal. Calcd. for $C_{14}H_{18}N_4O_3S$: C, 52.16; H, 5.63; N, 17.38; S, 9.95. Found: C, 51.92; H, 5.82; N, 17.04; S, 9.82.

EXAMPLE 3

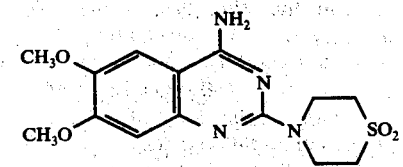

6,7-Dimethoxy-2-(4-thiomorpholinyl)-4-quinazolinamine S,S-Dioxide

A mixture of 9.40 g of 2-chloro-6,7-dimethoxy-4-quinazolinamine and 10.6 g of thiomorpholine S,S-dioxide in 200 ml of chlorobenzene was refluxed for 24 hrs. The reaction mixture was cooled to room temperature, and the precipitate was collected. There was deposited 9.10 g (61.1%) of white powder, mp 271°–275°, dec. Recrystallization from aqueous ethanol gave a pure product, mp 275°–276° dec.

Anal. Calcd. for $C_{14}H_{18}N_4O_4S.HCl$: C, 44.86; H, 5.11; Cl, 9.46; N, 14.95; S, 8.55. Found: C, 44.93; H, 5.13; Cl, 9.19; N, 14.83; S, 8.49.

As stated earlier, the compounds of this invention are suitably and generally administered in oral dosage form, such as by tablet or capsule, by combining the same in an effective amount with any oral pharmaceutically acceptable inert diluent, such as lactose, starch, dicalcium phosphate, calcium sulfate, kaolin, mannitol and powdered sugar. In addition, when required, suitable binders, lubricants, disintegrating agents, and coloring agents can also be added. Typical binders include starch, gelatin, sugars such as sucrose, molasses, and lactose, natural and synthetic gums such as acacia sodium alginate, extract of Irish moss, carboxymethyl cellulose, methylcellulose, and polyvinylpyrrolidone, polyethylene glycol, ethylcellulose, and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methyl cellulose, agar, bentonite, cellulose and wood products, alginic acid, guar gum, citris pulp, carboxymethyl cellulose, and sodium lauryl sulfate. If desired, conventionally pharmaceutically acceptable dyes such as any of the standard FD & C dyes may be incorporated into the dosage unit form.

From the foregoing description, one skilled in the art can easily ascertain the essential characteristics of this invention and without departing from the spirit and scope thereof can make various changes and/or modifications to the invention for adapting it to various usages and conditions. Accordingly, such changes and modifications are probably intended to be within the full range of equivalents of the following claims.

I claim:
1. Compounds of the general formula:

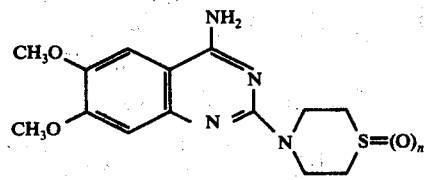

wherein n is 0, 1 or 2 and pharmaceutically acceptable salts thereof.

2. The compound according to claim 1 which is 6,7-dimethoxy-2-(4-thiomorpholinyl)-4-quinazolinamine.

3. The compound according to claim 1 which is 6,7-dimethoxy-2-(4-thiomorpholinyl)-4-quinazolinamine S-oxide.

4. The compound according to claim 1 which is 6,7-dimethoxy-2-(4thiomorpholinyl)-4-quinazolinamine S,S-dioxide.

5. A pharmaceutical composition comprising a pharmaceutical acceptable carrier in combination with a pharmaceutically effective amount of a compound or salt according to claim 1.

* * * * *